(12) United States Patent
Sarkozi et al.

(10) Patent No.: US 7,142,291 B2
(45) Date of Patent: Nov. 28, 2006

(54) DETECTION OF PARTIAL DISCHARGE OR ARCING IN WIRING VIA FIBER OPTICS

(75) Inventors: Janos Gyorgy Sarkozi, Niskayuna, NY (US); Nicole Andrea Evers, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 393 days.

(21) Appl. No.: 10/745,245

(22) Filed: Dec. 23, 2003

(65) Prior Publication Data

US 2005/0134837 A1 Jun. 23, 2005

(51) Int. Cl.
*G01N 21/00* (2006.01)
(52) U.S. Cl. .................................................. 356/73.1
(58) Field of Classification Search .............. None
See application file for complete search history.

(56) References Cited

U.S. PATENT DOCUMENTS

| 6,784,983 B1 * | 8/2004 | Bjerkan et al. ............ 356/73.1 |
| 2002/0130668 A1 | 9/2002 | Blades |

FOREIGN PATENT DOCUMENTS

| EP | 0788207 | 7/2000 |
| GB | 2388723 | 11/2003 |
| JP | 2269980 | 11/1990 |

OTHER PUBLICATIONS

Mangeret et al., "Optical Detection of Partial Discharges using Fluorescent Fiber," IEEE Transaction on Electrical Insulation, vol. 26 No. 4, Aug. 1991, pp. 783-789.
G. Guanzhong et al., "Monitoring System and Method for Wiring Systems", GE Application No. 124048; U.S. Appl. No. 10/063,603, filed May 3, 2002.
GB Search Report, GB0423319.3, Mar. 10, 2005.

* cited by examiner

*Primary Examiner*—Tu T. Nguyen
(74) *Attorney, Agent, or Firm*—Penny A. Clarke; Patrick K. Patnode (57) ABSTRACT

A cable, system and method for detecting partial discharges or arcing in wiring or cables via fiber optics are provided. The cable for detecting partial discharges includes a conductor for carrying electrical signals; at least one fluorescent optical fiber for detecting light generated by a partial discharge; and a first transparent layer surrounding the conductor for supporting the at least one fluorescent optical fiber generally parallel to the conductor. By employing a fluorescent optical fiber, incident light generated by a partial discharge along a length of the optical fiber will be transmitted via the optical fiber to an optical receiver for determining a partial discharge has occurred.

32 Claims, 9 Drawing Sheets

FIG. 1

OPTICAL CHARACTERISTICS:

| Parameters | Typical values |
|---|---|
| Refractive index | Core $n_1 = 1{,}592$ <br> Cladding $n_2 = 1{,}416$ |
| Numerical aperture (NA $= \sqrt{n_1^2 - n_2^2}$) | 0,73 |
| Acceptance angle (degrees) | 93 |

| Fluorescent fibre type | F205 | F200 | F201 | F203 | F204 | F202 |
|---|---|---|---|---|---|---|
| Absorption spectrum (nm) measured at half height | 294-410 | 315-410 | 299-477 | 388-511 | 441-545 | 493-580 |
| Re-emission spectrum (nm) measured at half height | 406-453 | 407-455 | 471-511 | 484-537 | 533-581 | 567-655 |
| Maximum emission peak (nm) | 424 | 427 | 493 | 520 | 542 | 625 |
| Colour | purple | blue | green | yellow | orange | red |

DETECTION OF PARTIAL DISCHARGE OR ARCING IN WIRING VIA FIBER OPTICS

GOVERNMENT INTERESTS

This invention was made with Government support under Contract No. N00014-02-C-0402 awarded by the Office of Naval Research. The Government has certain rights in this invention.

BACKGROUND OF THE INVENTION

This disclosure relates generally to systems and methods for detecting defects in aircraft wiring, and more particularly,.to systems and methods for detecting partial discharges or arcing in wiring or cables via fiber optics.

Wiring is a critical system in aircraft, shipboard, industry and home applications. Aircraft wiring integrity and safety related issues are known to be serious and have received a great deal of interest after the Swissair 111 and TWA 800 accidents. Also, electrical fires in industry account for a large portion of property loss, and electrical fires in the home are a significant portion of the fires occurring in the home that threaten life and damage property.

Aircraft wiring insulation is much thinner than that found in building wiring in order to reduce weight. This thin insulation deteriorates with age due to changes in chemical composition, vibration during flights, large temperature changes, and exposure to agents such as dust, salt, moisture and cleaning chemicals. This wiring is also exposed to other mechanical stresses during maintenance. The aforementioned effects will degrade the insulation, causing cracks and chafing. These insulation defects can cause arcing between wires or surrounding metals. Humidity together with salt and dust depositions can make the arc creation more probable.

The detection of aircraft wiring defects is primarily performed by visual inspection by maintenance personnel. This manual inspection is a slow process and its reliability is not satisfactory. Furthermore, as it requires twisting the wiring in order to visually check chafing, this visual inspection often causes more problems than it can identify.

There does exist test equipment on the market for wire and cable testing based on electrical measurements using Time Domain Reflectometry or Frequency Domain Reflectometry. The sensitivity of these methods is usually not satisfactory to detect all insulation damage.

General Dynamics of Redmond, Washington recently introduced a new test apparatus called the Micro-Energy Dielectric (MED) tool, as disclosed in U.S. patent application Publication No. US2002/0130668. This device uses a high DC voltage to generate discharges or arcs at insulation defects in a cable bundle under test. If a fault exists between the wire under test in the cable and any other grounded wires in the cable that has a breakdown voltage less than the maximum test voltage applied, the full discharge of the available charge stored in the cable, i.e., not a partial discharge, will occur at the fault. The location of the discharge is then determined in several ways by measuring the electromagnetic (i.e., RF region) and acoustic signals the discharge generates. First, the MED tool measures high frequency voltage pulse edges generated by the discharge at one end of the cable and determines the location of the discharge; second, a Electromagnetic Locating Tool (EML) measures the radiated (i.e., outside the cable) electromagnetic signal (radio waves) with receivers having suitable antennae and calculates the location of the discharge based on the arrival times of the signals at the receivers; and lastly, an Ultrasonic Locating Tool (ULT) measures the acoustic noise (i.e., sound waves) and the electromagnetic edge the discharge generates and determines the distance to the arc by timing the difference in arrival times of the two signals.

Therefore, a need exists for techniques to detect defects in wiring or cables that can be performed by other than visual inspection and will not cause further degradation to the wire or cable under test.

BRIEF DESCRIPTION OF THE INVENTION

Partial discharge (PD) testing is a sensitive, widely used method to characterize a condition of insulation materials. Partial discharges have much lower energy therefore degradation of the cable insulation material caused by the partial discharges during testing is negligible. In an embodiment of the present invention, fluorescent material-doped fiber optic cable(s) embedded in the wiring or cable is used to detect light generated during partial discharge activity or arcing. The fluorescent material-doped fiber optic cable collects this light and carries it to optical receivers, e.g., photomultipliers, at an end of the fluorescent-doped fiber optic cables embedded in the wiring.

According to an aspect of the present disclosure, a cable for detecting partial discharges is provided, the cable comprising a conductor for carrying electrical signals; at least one fluorescent optical fiber for detecting light generated by a partial discharge; and a first transparent layer surrounding the conductor for supporting the at least one fluorescent optical fiber generally parallel to the conductor.

According to another aspect, a system for detecting partial discharges comprises a cable comprising a conductor for carrying electrical signals; at least one fluorescent optical fiber for detecting light generated by a partial discharge; and a first insulation layer surrounding the conductor for supporting the at least one fluorescent optical fiber generally parallel to the conductor; a first optical receiver coupled to a first end of the cable for detecting light transmitted by the optical fiber by a partial discharge; a voltage source for inducing the partial discharge in the cable; and a processor for controlling operations of the voltage source and for determining if the first optical receiver has detected light.

According to a further aspect of the present disclosure, in a cable comprising a conductor for carrying electrical signals, at least one fluorescent optical fiber for detecting light generated by a partial discharge and a first insulation layer surrounding the conductor for supporting the at least one fluorescent optical fiber generally parallel to the conductor, a method for detecting partial discharges is provided. The method comprises the steps of applying a high voltage to the cable; and detecting light in the at least one fluorescent optical fiber generated by the partial discharge.

BRIEF DESCRIPTION OF THE DRAWINGS

The above and other aspects, features, and advantages of the present invention will become more apparent in light of the following detailed description when taken in conjunction with the accompanying drawings in which.

DETAILED DESCRIPTION OF THE INVENTION

Preferred embodiments of the present invention will be described hereinbelow with reference to the accompanying drawings. In the following description, well-known functions or constructions are not described in detail to avoid obscuring the invention in unnecessary detail. Throughout the figures, like reference numerals represent like elements.

The insulation condition of a wire, cable or cable bundle can be tested by partial discharge (PD) diagnostics or arcing. Electric discharges that do not completely bridge two electrodes or conductors in close proximity to each other are called partial discharges (PD). The magnitude of such discharges are usually small, the amount of charge transferred is in the range of ten to a few hundred Pico-Coulombs (pC). For a partial discharge test, a suitably high AC or DC voltage is applied to the conductors surrounding the insulation material under test. For cable diagnostics, the high voltage is applied between the wire under test (WUT) and the wires or shielding surrounding the wire under test. Alternatively, the high voltage is applied between the wire under test and a metal frame touching or potentially touching the wire under test, e.g., grounded metal structures. Alternatively, the discharge can be detected under normal current/voltage operating conditions depending on the defect and energized system characteristics.

When partial discharge occurs, the discharge will generate high frequency electrical signals traveling along the cable, electromagnetic radiation out of the cable, sound waves and light. Depending on the gas atmosphere and pressure at the location of the partial discharge, the spectral distribution of the light generated by the partial discharge varies. For air at atmospheric pressures, the spectral range is primarily in the UV and visible region. Partial discharges can be detected by any of the above-mentioned effects.

For cables, the most frequently used partial discharge detection method is to detect the high frequency electrical signal the partial discharge generates and propagates along the cable. The primary limitation of this method is that the high frequency signal is attenuated as it propagates along the cable making the detection of partial discharge pulses less likely, depending on the magnitude of the partial discharge pulses and the length and high frequency attenuation of the cable. The cable can also collect high frequency electromagnetic noise from the environment and that signal is merged with the partial discharge signal. Frequently, it is not possible to separate the attenuated partial discharge signal from the noise, thus reducing the sensitivity of the partial discharge detection.

Partial discharges also produce light and therefore it is possible to detect partial discharges by measuring the light generated by it. The primary problem with this method is that, in the case of a cable, the partial discharge occurs in the insulating material and the light generated is absorbed in the cable. Even if the cable has a transparent insulation material and the light generated by the partial discharge pulses is not absorbed by any other material in or around the cable, the light is locally generated and has to be detected by directly monitoring the location of the partial discharge generation.

To solve the problem associated with collection of the light generated by a partial discharge along the whole length of a cable, the application of a fluorescent optical fiber is provided which is able to collect light along its whole length.

For optical fibers used for communication or other light transmission applications, light is coupled into the optical fiber at one end and the light leaves the optical fiber at the other end. A typical optical fiber includes a core made of a higher reflective index material than that of the cladding surrounding the core. The core and cladding form a reflective interface that causes light beamed into the core to reflect off the surface where the two materials meet back into the core by the process of total internal reflection. However, there is a limited angle, e.g., the acceptance angle, measured from the axis of the optical fiber from within it is possible to couple the light into the optical fiber. Such fibers are not suitable to collect light along their length.

Figure 1:
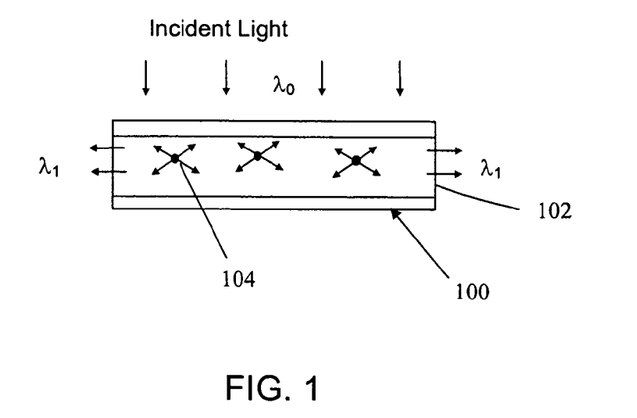
FIG. 1 illustrates a fluorescent optical fiber where incident light is absorbed and remitted at extremities of the optical fiber.

Referring to FIG. 1, an optical fiber 100 with fluorescent doping material in its core 102 is illustrated. If the fluorescent doping material embedded into the fiber core material 102 is excited by a light with suitable wavelengths illuminating the optical fiber, part of the emitted light from the fluorescent doping material will fall within the acceptance angle of the optical fiber and such light can propagate along the fiber. As long as the wavelengths of the incident light $\lambda_0$ fall within the absorption spectrum of the fluorescent material, photons 104 are absorbed and reemitted isotropically in the core, at longer wavelengths $\lambda_1$, i.e., the fluorescent light has longer wavelength than the light inducing the fluorescence. In this way, the fluorescent material in the core 102 can be illuminated by light rays coming from any incident angle, even through the side of the fiber, so that the orientation of the fiber axis relative to the discharge is no longer a constraint. It is preferable to utilize fluorescent doping materials that will not absorb the emitted light as it propagates along the fiber. This makes possible to detect partial discharge at a long distance away from its generation.

Figure 2:
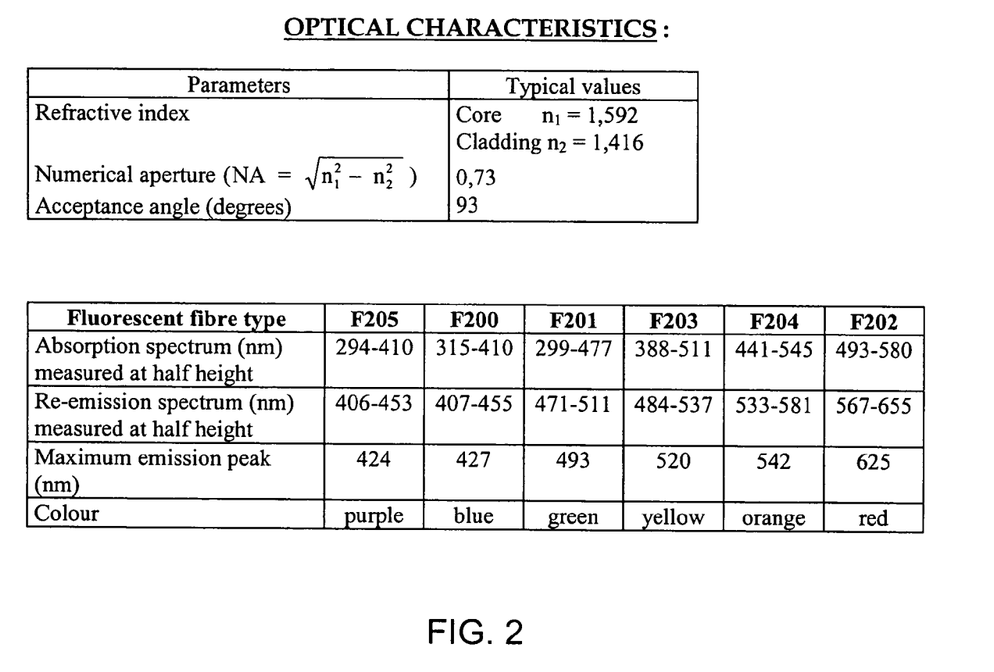
FIG. 2 illustrates optical characteristics of exemplary fluorescent optical fibers.

Exemplary fluorescent optical fibers are commercially available from Optectron Industries of Les Ulis Cedex, France. FIG. 2 illustrates the optical characteristics of these exemplary optical fibers.

To collect the light generated by the partial discharge activity, the partial discharge location must be visible by the fluorescent optical fiber. This can be achieved by surrounding the conductor wire with a material transparent (or partially transparent) for the light emitted by the partial discharge to be transmitted through. The fluorescent optical fibers are then embedded into the material surrounding the conductor wire. To be able to collect the light from the partial discharge, the excitation wavelength region of the fluorescent optical fiber must at least partially overlap with the wavelength region of the light generated by the partial discharge.

Figure 3:
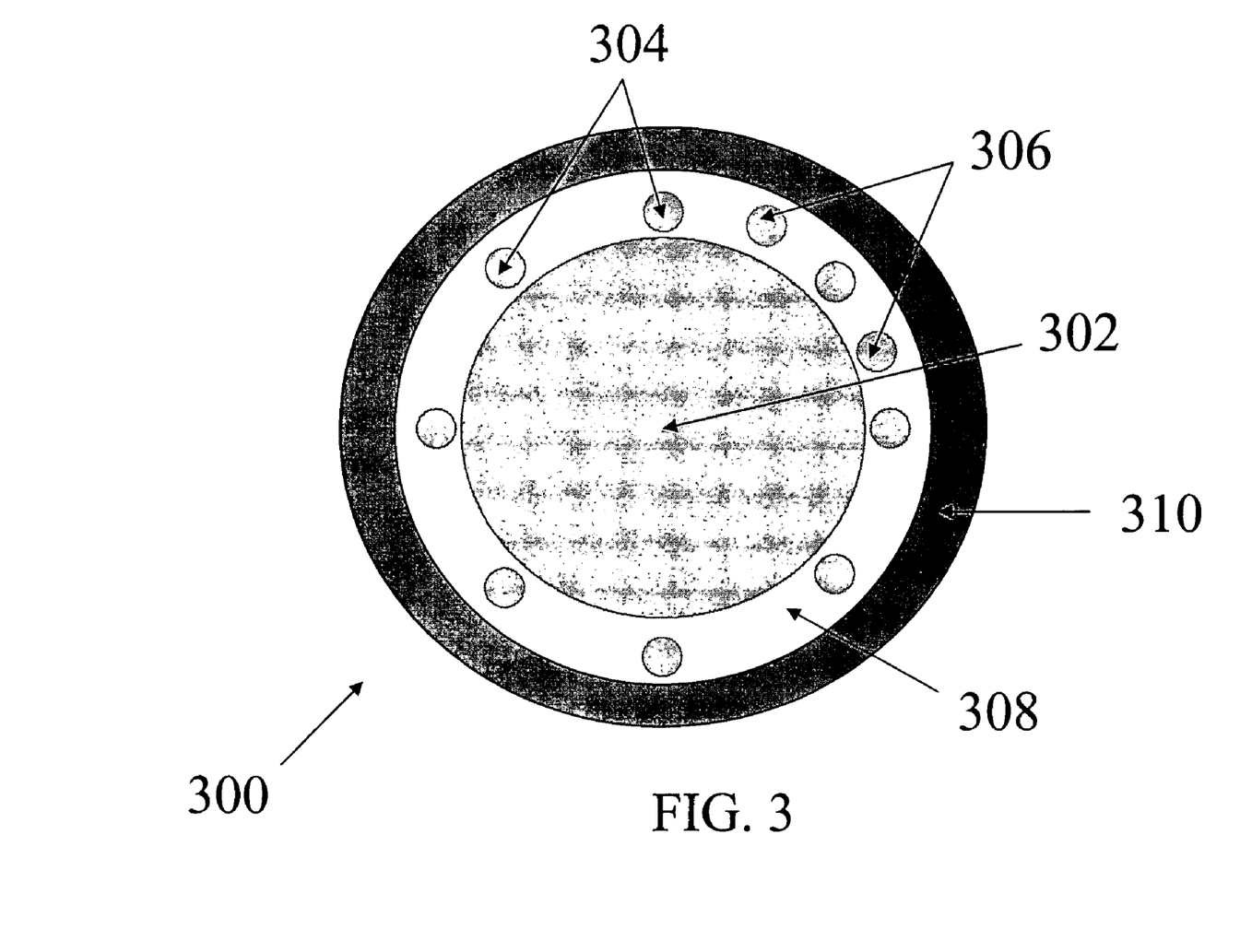
FIG. 3 illustrates an embodiment of a cable for detecting partial discharges.

Referring to FIG. 3, a cable for detecting partial discharges is illustrated. The cable 300 includes a conductive wire or conductor 302 for carrying electrical signals, e.g., data signals, power signals, etc. At least one fluorescent optical fiber 304 is located adjacent to the conductor 302 throughout the length of the cable 300. The at least one fluorescent optical fiber 304 is embedded into a transparent or semitransparent layer 308 surrounding the conductor 302. The transparent layer 308 is preferably an insulator and is transparent or semitransparent in the excitation wavelength region of the fluorescent optical fiber. The transparent layer 308 must be transparent or semitransparent at the excitation wavelength of the fluorescent optical fiber to allow the light generated by the partial discharge to reach the fluorescent optical fiber 304. Optionally, additional optical fibers 306 may be supported in the transparent layer 308 for data communication. The cable 300 also includes a second insulation layer 310 surrounding the conductor 302 and transparent material 308 supporting the optical fibers 304, 306. The second insulation layer 310 is composed of insulation material to provide the required electrical insulation and to protect the cable. The insulation material for the second insulation layer 310 is preferably non-transparent to prevent any light from outside the cable 300 from entering the fluorescent optical fiber 304, however, depending on the application, if no disturbing light can reach the fluorescent optical fibers 304 in the excitation wavelength region of the fluorescent optical fibers 304, transparent material can also be used.

It is to be appreciated the fluorescent optical fiber 304 includes a core of a first index of refraction, i1 surrounded by cladding of a second index of refraction, i2. By constructing the optical fiber with the core having a greater index of refraction than that of the cladding, light will propagate down the core by total internal reflection.

Figure 4:
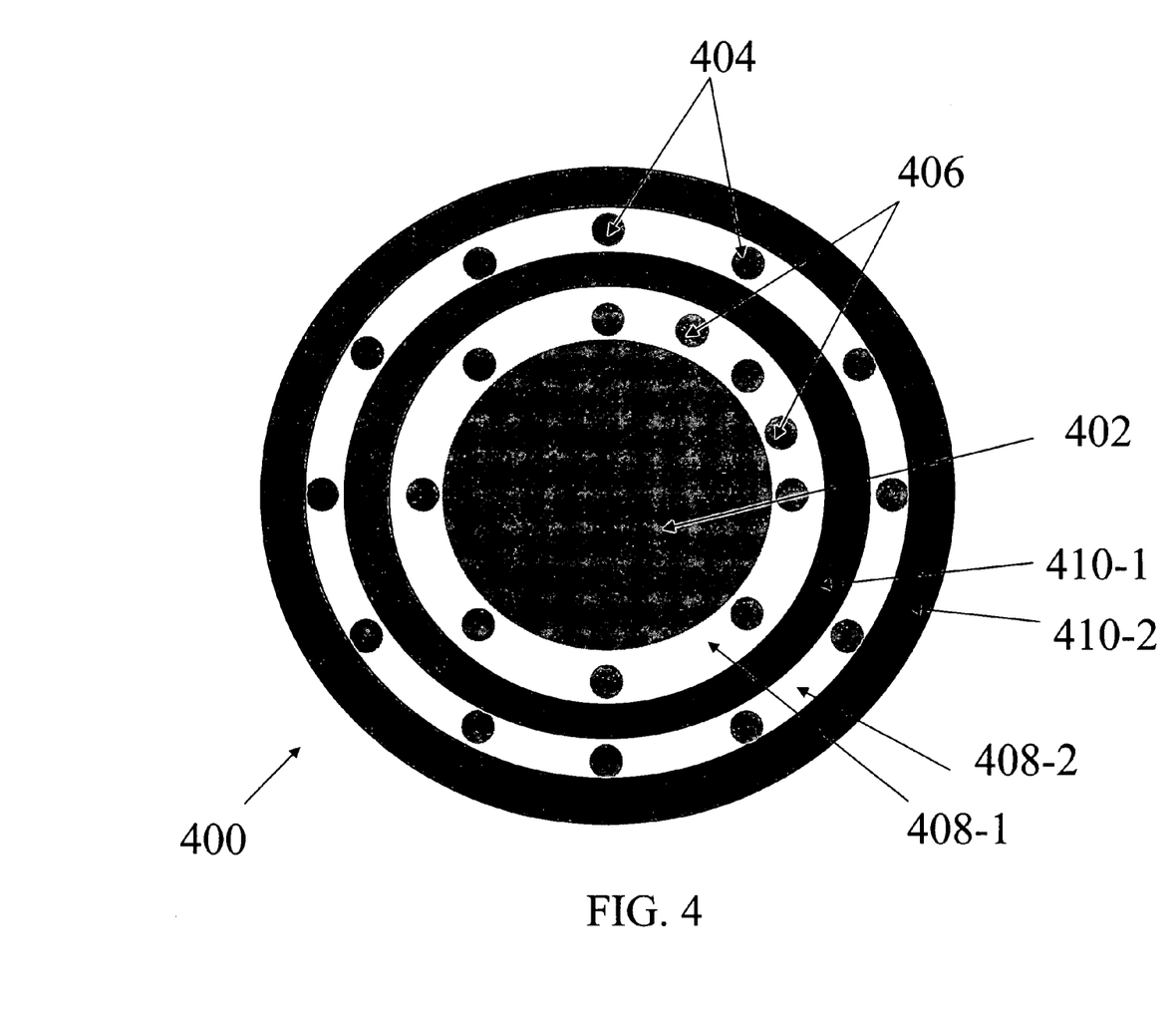
FIG. 4 illustrates another embodiment of a cable for detecting partial discharges.

FIG. 4 illustrates another embodiment of a cable for detecting partial discharges. The cable 400 includes a conductor 402, a first transparent or semitransparent layer 408-1, and a first insulation layer 410-1, which can be non-transparent. Any of the layers may include at least one optical fiber for communications 406. The cable 400 further includes a second transparent insulation layer 408-2 for supporting at least one fluorescent optical fiber 404 and a second non-transparent insulation layer 410-2. It is possible, that the first insulation layer may become cracked and, to some degree, conductive dust, etc. deposits into the crack. In this case, the partial discharge can be formed in between the insulation layers illuminating the outer fluorescent optical fibers 404 only.

Figure 5:
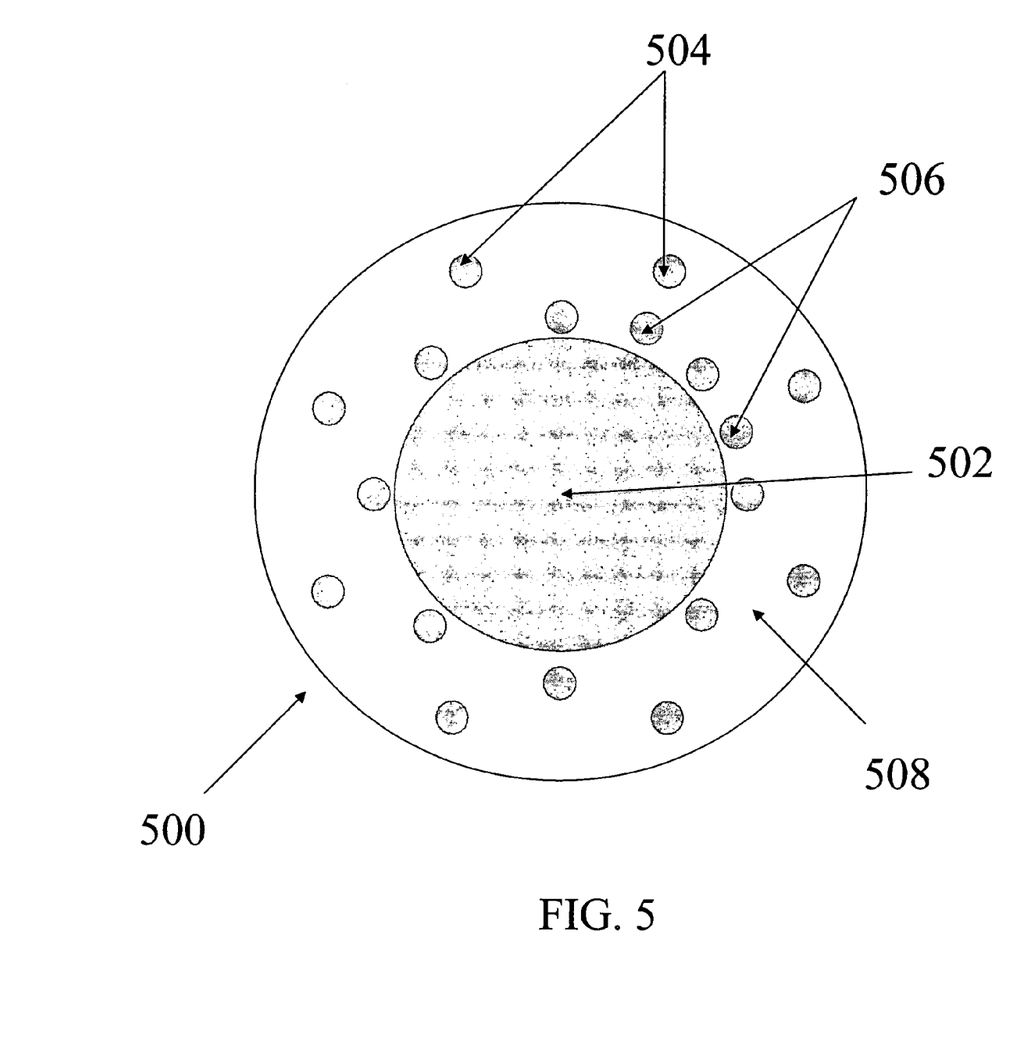
FIG. 5 illustrates yet another embodiment of a cable for detecting partial discharges.

Another embodiment of a cable for detecting partial discharges is shown in FIG. 5. The cable 500 of FIG. 5 includes a conductive wire or conductor 502 for carrying electrical signals and a transparent insulation layer 508 for supporting a plurality of fluorescent optical fibers 504. In this embodiment, the transparent insulation layer 508 provides all the required electrical insulation and mechanical protection for the cable. Optionally, additional optical fibers 506 may be supported in the layer 508 for data communication.

Figure 6:
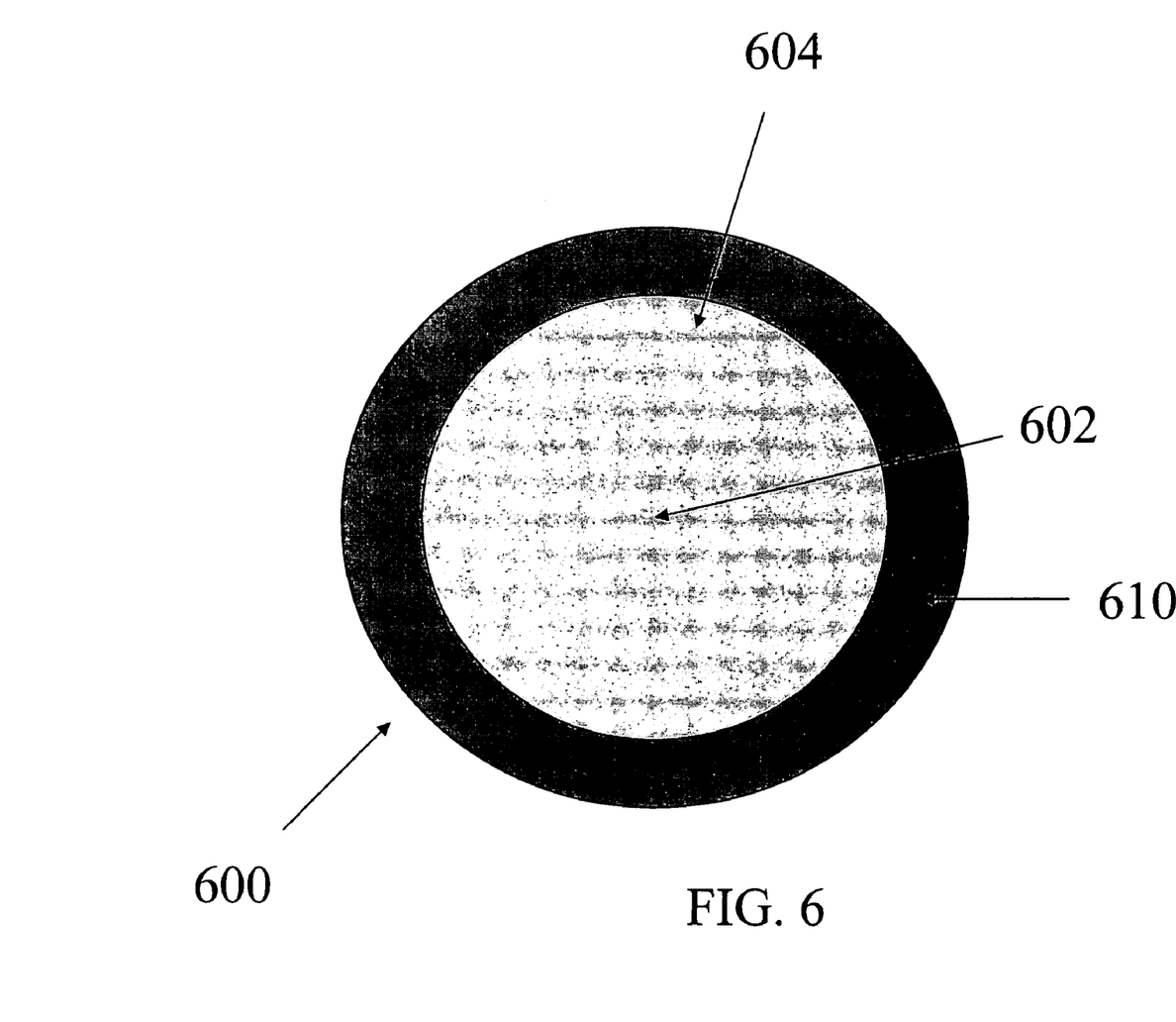
FIG. 6 illustrates a further embodiment of a cable for detecting partial discharges.

Referring to FIG. 6, a hollow optical fiber or waveguide 604 can be employed in another embodiment of a cable 600 for detecting partial discharges wherein a conductive wire 602 resides inside the hollow optical fiber 604. A layer of non-transparent insulation 610 may surround the hollow optical fiber 604 to provide sufficient electrical insulation, mechanical protection and if required to prevent light generated outside the cable 600 from entering the optical fiber 604.

Figure 7:
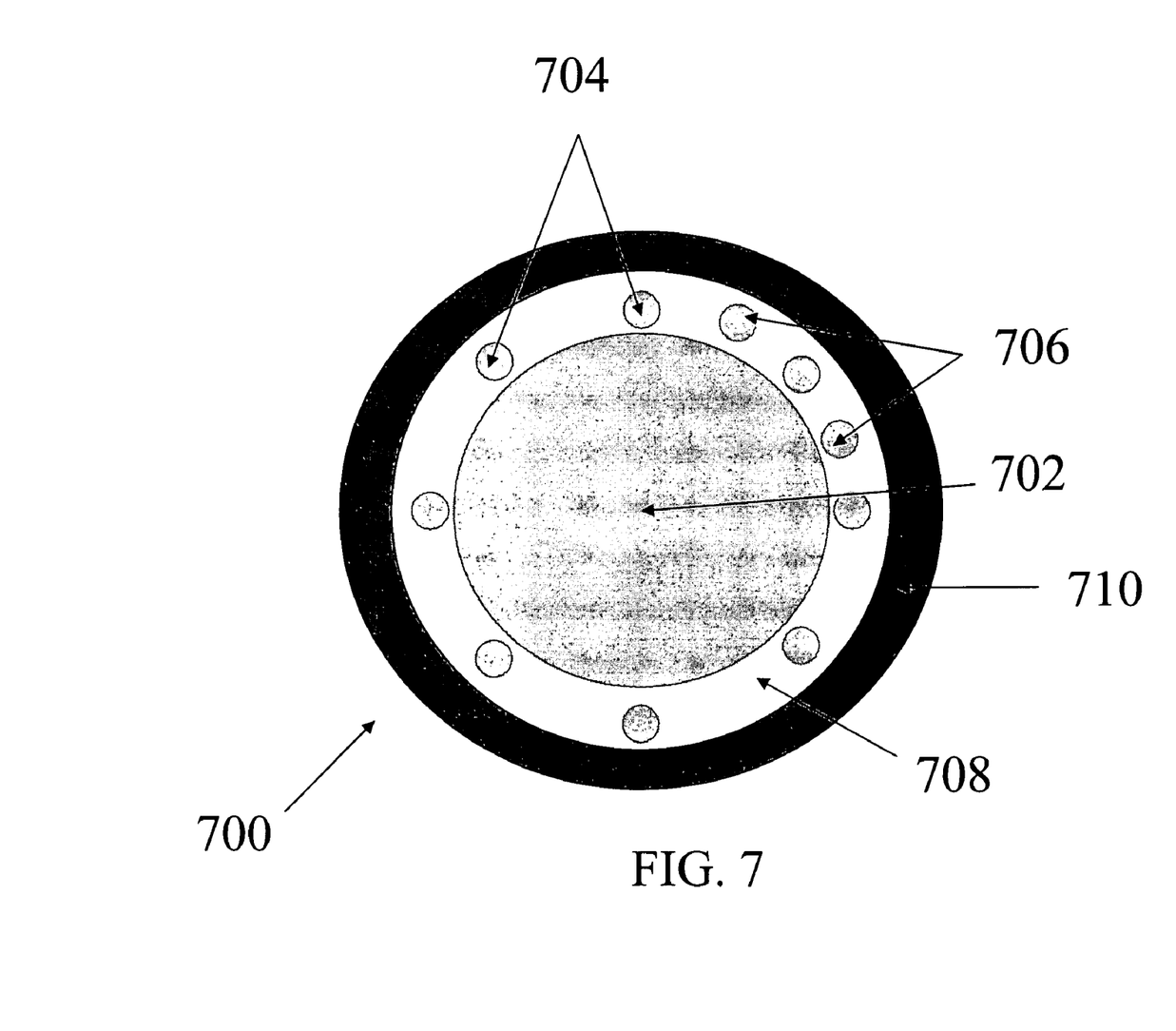
FIG. 7 illustrates a still further embodiment of a cable for detecting partial discharges.

FIG. 7 illustrates an embodiment of a cable 700 for detecting partial discharges similar to the embodiment shown in FIG. 3. Cable 700 includes a conductive wire or conductor 702 for carrying electrical signals and at least one fluorescent optical fiber 704 for detecting light generated by a partial discharge. However, the fluorescent optical fiber 704 does not include a cladding layer for reflecting light into the optical fiber. In this embodiment, insulation layer 708 is made from a cladding material. By employing cladding material in the insulation layer 708, the manufacture of the optical fiber can be simplified, e.g., only the core needs to be fabricated. Furthermore, the cable 700 may include at least one communication optical fiber 706. The cable may be surrounded by a non-transparent insulation material 710 to provide sufficient electrical insulation, mechanical protection and if required to prevent light generated from outside the cable from entering the fluorescent optical fiber 704.

In various embodiments, the fluorescent optical fiber can also be used in gas insulated transmission lines, transformers, switchgears or any other high voltage applications where light generated by a partial discharge or other discharge processes, requires distributed light sensing.

Partial discharge can be generated by any degradation in the insulation material (e.g. chafing, crack in the insulation material), but partial discharges are not always produced at the voltage level occurring in the wiring under operating conditions. In this case, the optical fibers around the cable can be used to monitor the integrity of the insulation. In this case, in normal operation, light is coupled into one or more fibers at one end of the fiber(s). The light intensity is measured at the other end of the fiber(s) with suitable optical detector(s). If damage occurs, it would result in increased or total attenuation of the conducted light intensity from one or more optical fibers. This increased attenuation can used to identify mechanical damage to the wire.

Since fluorescent optical fibers can be used to conduct light in the wavelengths regions not absorbed by the doping material, the fluorescent optical fibers in the cable can also be used for information transmission as it is widely used with non-fluorescent optical fibers. The absorption and fluorescent wavelength region of the fluorescent optical fibers has to be selected in a way to avoid overlap with the communication signal wavelength(s) (or vice versa). This way any interference can be eliminated between the communication signal and the light generated by the detected discharge activity. In this case, the partial discharge signal and the communication signal will appear at different wavelength at the end of the fiber(s) and can be detected by detectors sensitive either at the communication or the fluorescent wavelength respectively.

Figure 8:
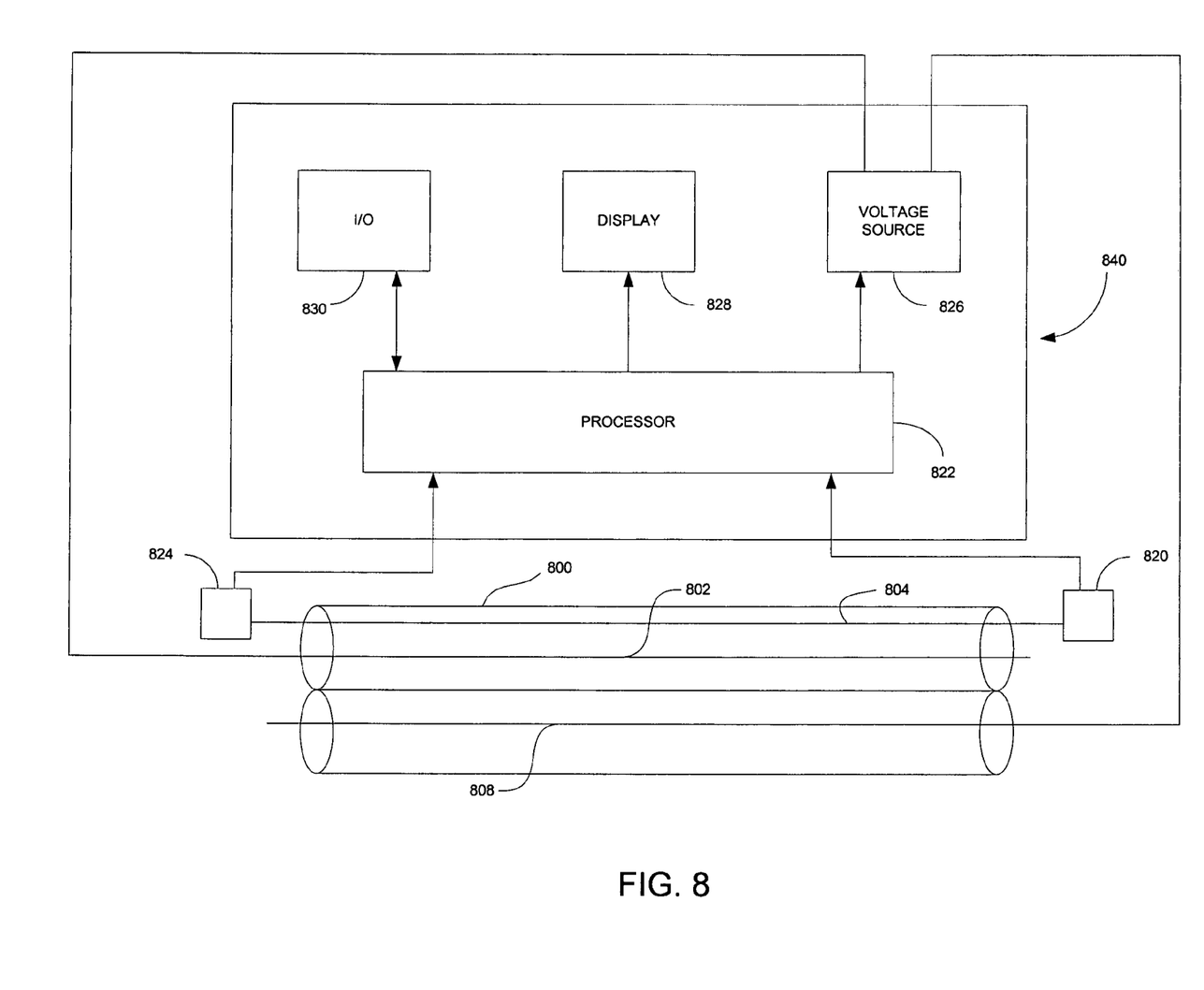
FIG. 8 is an exemplary system for detecting partial discharges.
Figure 9:
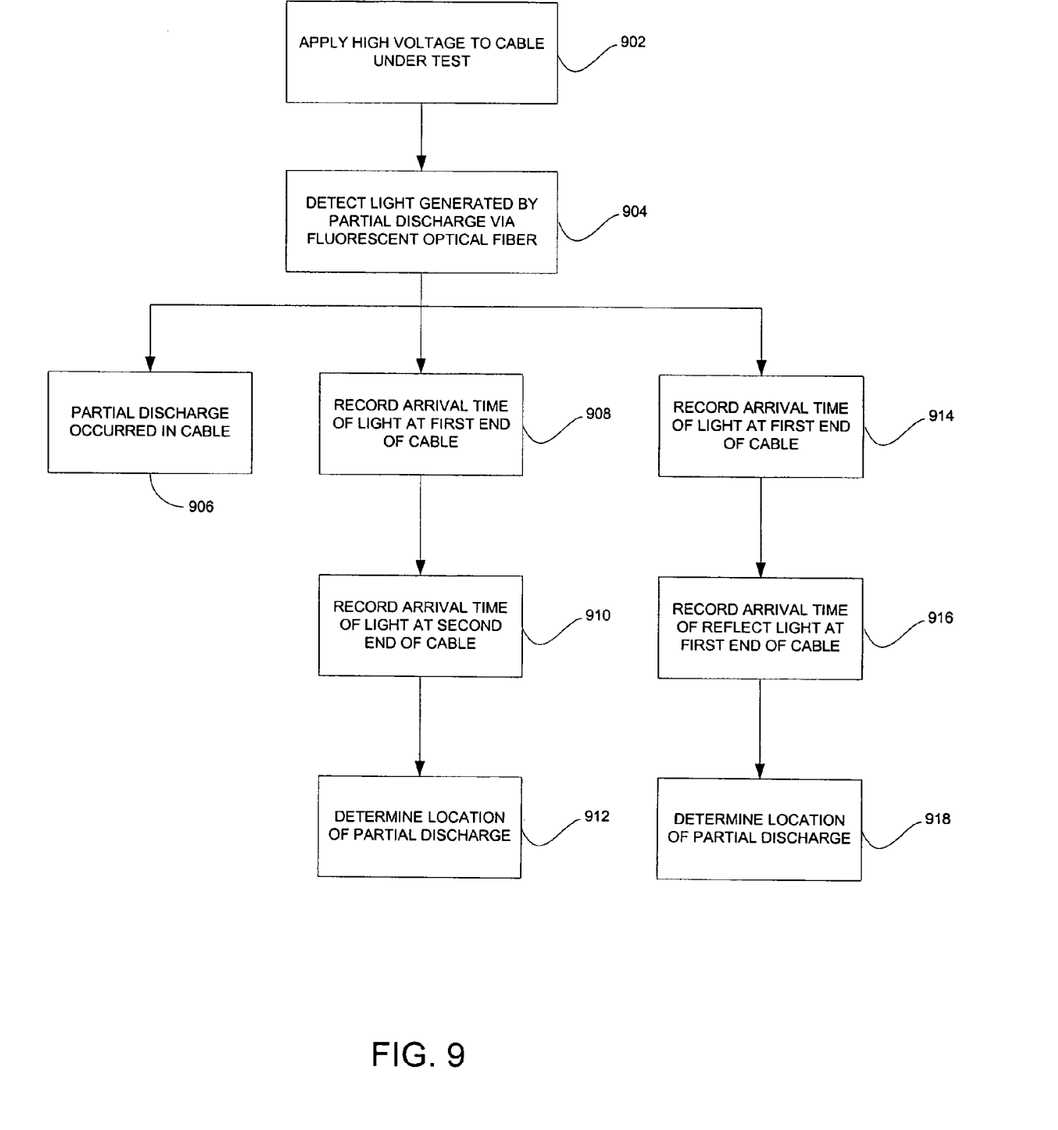
FIG. 9 is a flowchart illustrating a method for detecting partial discharges in a cable via fiber optics.

Referring to FIGS. 8 and 9, an exemplary system and method for detecting partial discharges in a cable via optical fibers will be described.

The system 840 includes cable 800 which further includes conductor 802 for carrying electrical signals and at least one optical fiber for detecting partial discharges 804. An optical receiver 820, e.g., a photomultiplier, photodiode, is coupled to at least one end of the cable 800 for detecting light transmitted via the optical fiber 804 from a partial discharge. Optionally, a second optical receiver 824 is coupled to the other end of the optical fiber 804 and is employed in certain methods for detecting partial discharges which will be described below. The optical receivers 820, 824 are coupled to a processor 822 for determining the presence and in certain embodiments the location of the partial discharge. The system further includes a voltage source 826 for applying a high voltage to the conductor 802 and an adjacent conductor 808 to induce partial discharges under testing conditions. In other implementations, the voltage source is not required, as the wire under test in normal operation mode will have suitable potential difference compared to its environment to induce partial discharges in case of insulation failure. Additionally, the system 800 includes a display 828 for displaying whether a partial discharge has occurred and the location of the partial discharge and an input/output interface 830 for controlling the system 800.

Initially, the system 800 will apply a high voltage to the conductors 802, 808 to induce a partial discharge (step 902). While the high voltage is being applied, the at least one optical receiver 820 will be activated by the processor to detect any light generated in the optical fiber 804 (step 904). In one embodiment of the method, the at least one optical detector 820 will detect a partial discharge, e.g., a short light pulse, has occurred in the cable 800 without indicating a location of the partial discharge (step 906).

Figure 10:
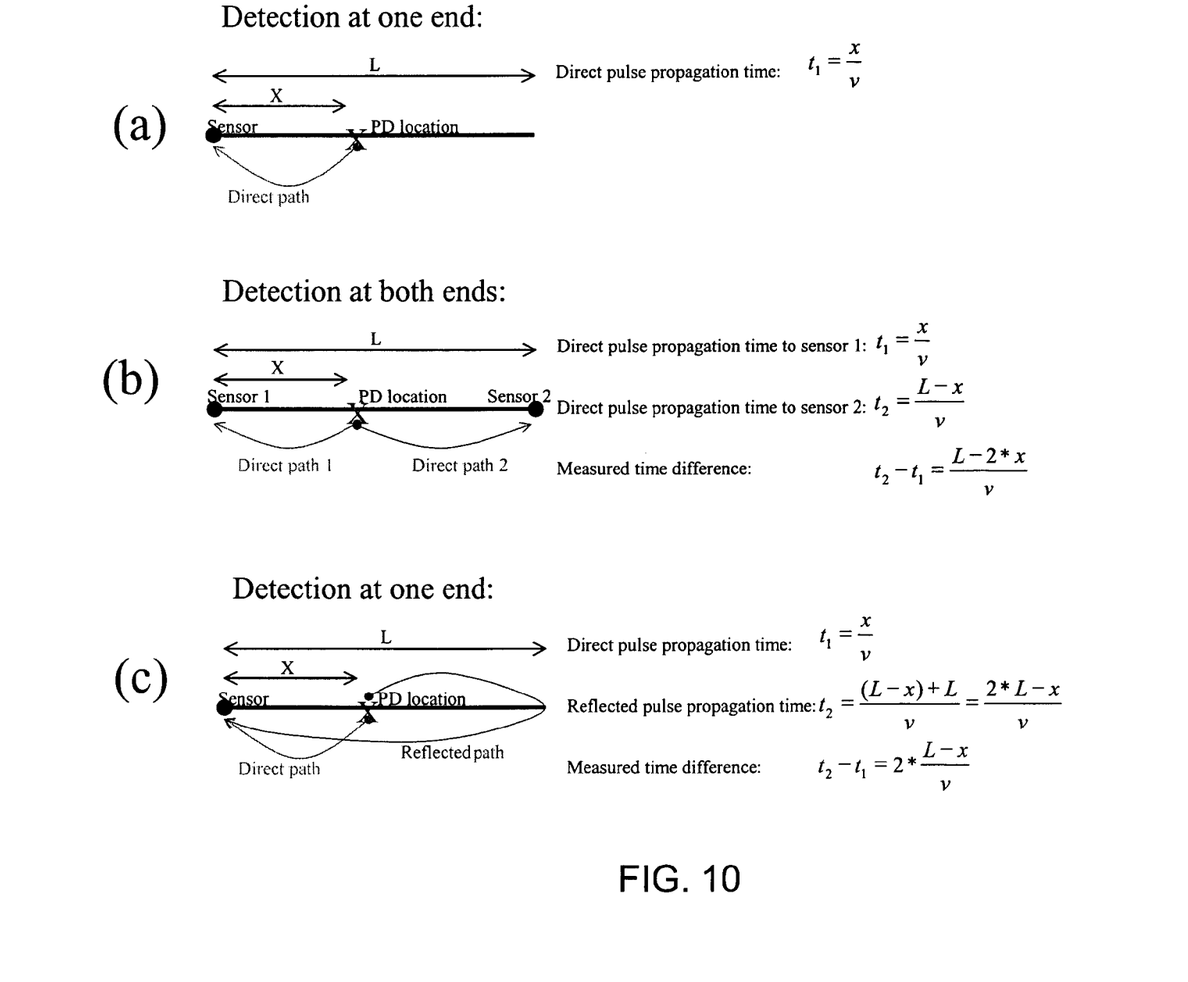
FIG. 10 illustrates several methods for determining a location of a partial discharge.

However, the location of the partial discharge may be calculated as shown in FIG. 10(*a*) where x is the distance to the defect, L is the length of wire and t1 is the arrival time of the pulse at the end of the fiber.

In another embodiment of the method for detecting partial discharges, the optical receiver 820 will detect a light pulse indicative of a partial discharge and record a time of the pulse via processor 822 (step 908). Similarly, optical receiver 824 will detect a light pulse indicative of the partial discharge and record a time of the pulse via processor 822 (step 910). If the light pulse is detected at both ends of the cable, processor 822 can determine the exact location of the source of the light pulse (step 912). For the location determination, the time difference between the arrival of the same light pulse to the two ends of the cable has to be measured, as shown in FIG. 10(*b*). The speed of light propagation in the optical fiber and the length of the fiber must be known to calculate the location. The formulae shown in FIG. 10(*b*) are then employed to calculate the location where x is the distance to defect; L is length of wire(and fiber); v is the speed of light propagation in the optical fiber; and t1, t2 are the arrival times of the pulses to the fiber ends, t1 and t2 measured from an arbitrary starting moment as only their difference is used for location calculation.

In yet another embodiment, the optical receiver 820 detects a light pulse and records it time of arrival (step 914). The optical receiver 820 then detects the light pulse reflected back from the other end of the optical fiber and measures the time the reflected pulse arrives (step 916). The processor 822 then determines the location using the arrival times of the pulses, the length of the cable and speed of light propagation in the optical fiber (step 918), as illustrated in FIG. 10(*c*).

Embodiments of the present disclosure can be used to build wiring with both electrical and optical signal transmission capabilities as well as the ability to detect and diagnose wire/cable defects. This wiring would provide enhanced signal transmission capabilities to applications ranging from aircraft wiring to home wiring with improved wiring defect diagnostics.

While the disclosure has been illustrated and described in typical embodiments, it is not intended to be limited to the details shown, since various modifications and substitutions can be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A cable for detecting partial discharges, the cable comprising:
   a conductor for carrying electrical signals;
   at least one fluorescent optical fiber for detecting light generated by a partial discharge; and
   a first transparent layer surrounding the conductor for supporting the at least one fluorescent optical fiber generally parallel to the conductor.

2. The cable as in claim 1, further comprising a first insulation layer for providing electrical insulation and protecting the cable.

3. The cable as in claim 2, wherein the first insulation layer is non-transparent.

4. The cable as in claim 2, further comprising a second insulation layer surrounding the conductor located between the conductor and the at least one fluorescent optical fiber.

5. The cable as in claim 4, wherein the second insulation layer is non-transparent.

6. The cable as in claim 4, further comprising a third insulation layer surrounding the first transparent layer for protecting the cable, the third insulation layer being non-transparent.

7. The cable as in claim 6, further comprising a fourth insulation layer located between the conductor and the second insulation layer.

8. The cable as in claim 1, further comprising at least one communication optical fiber for carrying data signals, the at least one communication optical fiber being supported by the first transparent layer generally parallel to the conductor.

9. The cable as in claim 1, wherein the first transparent layer is an insulator.

10. The cable as in claim 1, wherein the at least one fluorescent optical fiber comprises a fluorescent-doped core having a first index of refraction and a cladding surrounding the core having a second index of refraction, wherein the first index of refraction is greater than the second index of refraction.

11. The cable as in claim 1, wherein the at least one fluorescent optical fiber is hollow and surrounds the conductor, the at least one hollow fluorescent optical fiber being located between the conductor and a first insulation layer.

12. The cable as in claim 11, wherein the first insulation layer is non-transparent.

13. The cable as in claim 1, wherein the at least one fluorescent optical fiber comprises a core having a first index of refraction and the first transaprent layer comprises cladding material having a second index of refraction.

14. A cable for detecting partial discharges, the cable comprising
   a conductor for carrying electrical signals;
   at least one fluorescent optical fiber for detecting light generated by a partial discharge;
   a first transparent layer surrounding the conductor for supporting the at least one fluorescent optical fiber generally parallel to the conductor;
   a first insulation layer for providing electrical insulation and protecting the cable;
   a second insulation layer surrounding the conductor located between the conductor and the at least one fluorescent optical fiber;
   a third insulation layer surrounding the first transparent layer for protecting the cable, the third insulation layer being non-transparent;
   a fourth insulation layer located between the conductor and the second insulation layer; and
   at least one communication optical fiber for carrying data signals, the at least one communication optical fiber being supported by the fourth insulation layer generally parallel to the conductor.

15. A system for detecting partial discharges, the system comprising:
a cable comprising:
a conductor for carrying electrical signals;
at least one fluorescent optical fiber for detecting light generated by a partial discharge; and
a first insulation layer surrounding the conductor for supporting the at least one fluorescent optical fiber generally parallel to the conductor;
a first optical receiver coupled to a first end of the cable for detecting light transmitted by the optical fiber by a partial discharge;
a second optical receiver coupled to a second end of the cable for detecting light generated by the partial discharge;
a voltage source for inducing the partial discharge in the cable; and
a processor for controlling operations of the voltage source and for determining if the first optical receiver has detected light, wherein the processor is adapted to determine a location of the partial discharge by arrival times of the light at the first and second optical receivers.

16. The system as in claim 15, wherein the cable further comprises a second insulation layer for protecting the cable.

17. The system as in claim 16, wherein the second insulation layer of the cable is non-transparent.

18. The system as in claim 15, wherein the cable further comprises at least one communication optical fiber for carrying data signals, the at least one communication optical fiber being supported by the first insulation layer generally parallel to the conductor.

19. The system as in claim 15, wherein the first insulation layer of the cable is transparent.

20. The system as in claim 15, wherein the at least one fluorescent optical fiber comprises a fluorescent-doped core having a first index of refraction and a cladding surrounding the core having a second index of refraction, wherein the first index of refraction is greater than the second index of refraction.

21. The system as in claim 15, wherein the cable further comprises a second insulation layer surrounding the conductor located between the conductor and the at least one fluorescent optical fiber.

22. The system as in claim 21, wherein the second insulation layer is non-transparent.

23. The system as in claim 21, wherein the cable further comprises a third insulation layer surrounding the first insulation layer for protecting the cable, the third insulation layer being non-transparent.

24. The system as in claim 23, wherein the cable further comprises a fourth insulation layer located being the conductor and the second insulation layer.

25. The system as in claim 24, wherein the cable further comprises at least one communication optical fiber for carrying data signals, the at least one communication optical fiber being supported by the fourth insulation layer generally parallel to the conductor.

26. The system as in claim 15, wherein the at least one fluorescent optical fiber is hollow and surrounds the conductor, the at least one hollow fluorescent optical fiber being located between the conductor and the first insulation layer.

27. The system as in claim 26, wherein the first insulation layer is non-transparent.

28. The system as in claim 15, wherein the at least one fluorescent optical fiber comprises a core having a first index of refraction and the first insulation layer comprises cladding material having a second index of refraction.

29. A system for detecting partial discharges, the system comprising:
a cable comprising:
a conductor for carrying electrical signals;
at least one fluorescent optical fiber for detecting light generated by a partial discharge; and
a first insulation layer surrounding the conductor for supporting the at least one fluorescent optical fiber generally parallel to the conductor;
a first optical receiver coupled to a first end of the cable for detecting light transmitted by the optical fiber by a partial discharge;
a voltage source for inducing the partial discharge in the cable; and
a processor for controlling operations of the voltage source and for determining if the first optical receiver has detected light, wherein the processor is adapted to determine an arrival time of the light at the first optical receiver and a reflected arrival time of the light being reflected from an end of the cable opposite to the end where the optical receiver is located and to determine a location of the partial discharge by the arrivals times of the light and reflected light.

30. In a cable comprising a conductor for carrying electrical signals, at least one fluorescent optical fiber for detecting light generated by a partial discharge and a first insulation layer surrounding the conductor for supporting the at least one fluorescent optical fiber generally parallel to the conductor, a method for detecting partial discharges, the method comprising the steps of:
applying a high voltage to the cable;
detecting light in the at least one fluorescent optical fiber generated by the partial discharge;
detecting the light generated at a first end of the cable and recording the light's arrival time at the first end;
detecting the light generated at a second end of the cable and recording the light's arrival time at the second end; and
determining a location of the partial discharge from the first and second arrival times of the light.

31. The method as in claim 30, further comprising the step of detecting the light by an optical receiver coupled to the at least one fluorescent optical fiber.

32. In a cable comprising a conductor for carrying electrical signals, at least one fluorescent optical fiber for detecting light generated by a partial discharge and a first insulation layer surrounding the conductor for supporting the at least one fluorescent optical fiber generally parallel to the conductor, a method for detecting partial discharges, the method comprising the steps of:
applying a high voltage to the cable;
detecting light in the at least one fluorescent optical fiber generated by the partial discharge;
detecting the light generated at a first end of the cable and recording the light's arrival time at the first end;
detecting the light reflect from a second end of the cable and recording the light's arrival time at the first end of the cable; and
determining a location of the partial discharge from the first and reflected arrival times of the light.

* * * * *